(12) United States Patent
Feldman et al.

(10) Patent No.: US 9,397,639 B2
(45) Date of Patent: Jul. 19, 2016

(54) INTEGRATED CIRCUITRY FOR GENERATING A CLOCK SIGNAL IN AN IMPLANTABLE MEDICAL DEVICE

(71) Applicant: Boston Scientific Neuromodulation Corporation, Valencia, CA (US)

(72) Inventors: Emanuel Feldman, Simi Valley, CA (US); Goran N. Marnfeldt, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 158 days.

(21) Appl. No.: 14/077,666

(22) Filed: Nov. 12, 2013

(65) Prior Publication Data
US 2014/0266375 A1 Sep. 18, 2014

Related U.S. Application Data

(60) Provisional application No. 61/784,082, filed on Mar. 14, 2013.

(51) Int. Cl.
| | |
|---|---|
| G06F 1/04 | (2006.01) |
| H03K 3/03 | (2006.01) |
| A61N 1/36 | (2006.01) |
| H03K 3/011 | (2006.01) |
| H03K 3/027 | (2006.01) |
| A61N 1/05 | (2006.01) |

(52) U.S. Cl.
CPC .............. *H03K 3/03* (2013.01); *A61N 1/36125* (2013.01); *H03K 3/011* (2013.01); *H03K 3/027* (2013.01); *A61N 1/0526* (2013.01); *A61N 1/0551* (2013.01)

(58) Field of Classification Search
CPC ............... G06F 1/10; G06F 1/04; G06F 1/08; H03K 5/135; H03K 5/132; G11C 7/22; H04L 7/0083
USPC .................................. 327/291–294, 298, 299
See application file for complete search history.

(56) References Cited

U.S. PATENT DOCUMENTS

| | | |
|---|---|---|
| 5,670,915 A | 9/1997 | Cooper et al. |
| 5,956,289 A | 9/1999 | Norman et al. |
| 6,052,035 A | 4/2000 | Nolan et al. |

(Continued)

OTHER PUBLICATIONS

"555 Timer IC," http://en. wikipedia.org/wiki/555_timer (Feb. 13, 2013).
"Relaxation Oscillators," http://mysite.du.edu/~etuttle/electron/elect10.htm (Feb. 11, 2013).
"LMC555 CMOS Timer" Data Sheet (2000).
International Search Report and Written Opinion regarding PCT Application No. PCT/US2013/069900, dated Feb. 24, 2014, 9 pages.

*Primary Examiner* — Lincoln Donovan
*Assistant Examiner* — Diana J Cheng
(74) *Attorney, Agent, or Firm* — Lewis, Reese & Nesmith, PLLC

(57) ABSTRACT

Timer circuitry completely formable in an integrated circuit (IC) for generating a clock signal in an implantable medical device is disclosed. The timer circuitry can be formed on the same Application Specific Integrated Circuit typically used in the implant, and requires no external components. The timer circuitry comprises modification to a traditional astable timer circuit. A resistance in the disclosed timer circuit can be trimmed to adjust the frequency of the clock signal produced, thus allowing that frequency to be set to a precise value during manufacturing. Precision components are not needed in the RC circuit, which instead are used to set the rough value of the frequency of the clock signal. A regulator produces a power supply for the timer circuitry from a main power supply (Vcc), producing a clock signal with a frequency that is generally independent of temperature and Vcc fluctuations.

31 Claims, 9 Drawing Sheets

(56) References Cited

U.S. PATENT DOCUMENTS

| | | | |
|---|---|---|---|
| 7,166,994 B2 * | 1/2007 | Lee et al. | 323/313 |
| 8,847,689 B2 * | 9/2014 | Zhao et al. | 330/311 |
| 2002/0035383 A1 | 3/2002 | Thompson | |
| 2003/0030499 A1 | 2/2003 | Huang et al. | |
| 2012/0095519 A1 | 4/2012 | Parramon et al. | |

* cited by examiner

US 9,397,639 B2

INTEGRATED CIRCUITRY FOR GENERATING A CLOCK SIGNAL IN AN IMPLANTABLE MEDICAL DEVICE

CROSS REFERENCE TO RELATED APPLICATIONS

This is a non-provisional of U.S. Patent Application Ser. No. 61/784,082, filed Mar. 14, 2013, which is incorporated herein by reference and to which priority is claimed.

FIELD OF THE INVENTION

The present invention relates generally to implantable medical devices, and more particularly to timer circuitry completely formable in an integrated circuit (IC) for generating a clock signal in an implantable medical device.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system. However, the present invention may find applicability in any implantable medical device system.

As shown in FIG. 1, a SCS system typically includes an Implantable Pulse Generator (IPG) 10, which includes a biocompatible device case 12 formed of titanium for example. The case 12 typically holds the circuitry and battery 26 necessary for the IPG to function, although IPGs can also be powered via external RF energy and without a battery. The IPG 10 is coupled to electrodes 16 via one or more electrode leads (two such leads 19 and 20 are shown), such that the electrodes 16 form an electrode array 22. The electrodes 16 are carried on a flexible body 24, which also houses the individual signal wires 27 coupled to each electrode. In the illustrated embodiment, there are eight electrodes on lead 19, labeled E1-E8, and eight electrodes on lead 20, labeled E9-E16, although the number of leads and electrodes is application specific and therefore can vary. The leads 19 and 20 couple to the IPG 100 using lead connectors 28, which are fixed in a header material 30 comprising an epoxy for example. Two coils (antennas) are generally present in the IPG 100: a telemetry coil 13 used to transmit/receive data to/from an external controller; and a charging coil 18 (inside case 12) for charging or recharging the IPG's battery 14 using an external charger.

FIG. 2 shows an Application Specific Integrated Circuit (ASIC) 300 used in an IPG such as IPG 10, which is disclosed in FIG. 4B of U.S. Patent Application Publication 2012/0095519, which is incorporated herein by reference. The same element numerals as disclosed in the '519 Publication are used in current FIG. 2, and the reader can refer to that publication for a more thorough description of ASIC 300. Generally speaking, the ASIC 300 attempts to integrate as much of the functionality in the IPG 10 as possible in a single Integrated Circuit (IC). Thus, the ASIC 300 includes different modules for controlling operation of various functions within the IPG, such as: charging/protection circuitry 64 for receiving energy from the charging coil 18 and using that energy to charge the IPG's battery 26; telemetry circuitry 62 coupled to the telemetry coil 13 to send and receive data externally from the IPG 10; stimulation circuitry 175 for forming the stimulation pulses to be provided to the electrodes, etc. It is not necessary here to describe the full functionality of ASIC 300.

What is important to note is that the ASIC 300 requires a clock signal to function. Typically, and as shown in FIG. 2, the clock signal was provided to the ASIC 300 by a crystal oscillator 340 at a clock input pin (CLKIN) on the ASIC. As is well known, a crystal 340 is a piezoelectric material that when biased resonates to create a signal with a very precise frequency. The frequency produced by the crystal 340 has a low temperature coefficient—meaning that it does not change significantly with temperature—and has a low frequency drift over time. Thus, a crystal 340 provides a stable clock signal, CLK, of a predictable frequency to the ASIC 300.

The inventors realize that use of a crystal 340 to provide a clock signal has disadvantages. As a discrete electro-mechanical device, the crystal 340 cannot be fully integrated into the ASIC 300. This is unfortunate, because the crystal 340 takes up some room on the printed circuit board (PCB; not shown) within the IPG, which room is ever-diminishing as IPGs are made smaller. A crystal 340 is also subject to mechanical damage, and can be susceptible to circuit parasitics present on the PCB, which can affect start-up time and performance. A crystal 340 is also slow to start, i.e., it takes some time (e.g., 15 seconds) to start producing its predictable frequency, which is undesirable in an application as critical as a medical implant. Moreover, the crystal 340, being a discrete component, adds cost to the manufacture of the IPG 10.

DETAILED DESCRIPTION

The inventors thus realize that it would be beneficial to produce a clock signal on the ASIC 300 itself in a solution that does not involve an external crystal or any other external precision devices located off of the ASIC. However, it is important that integrated clocking circuitry on the ASIC 300 be capable of producing a clock signal that does not vary appreciably with temperature. This can be difficult to achieve because the transistors traditionally used in integrated circuitry will inherently vary in their performance with temperature. It is also preferable that the clock signal produced has a precise frequency. This can also be difficult to achieve because variability in manufacturing of the ASIC 300 can cause slight differences in the electrical parameters comprising the clocking circuitry, and hence can affect the frequency of the clock signal from chip to chip.

Figure 1:
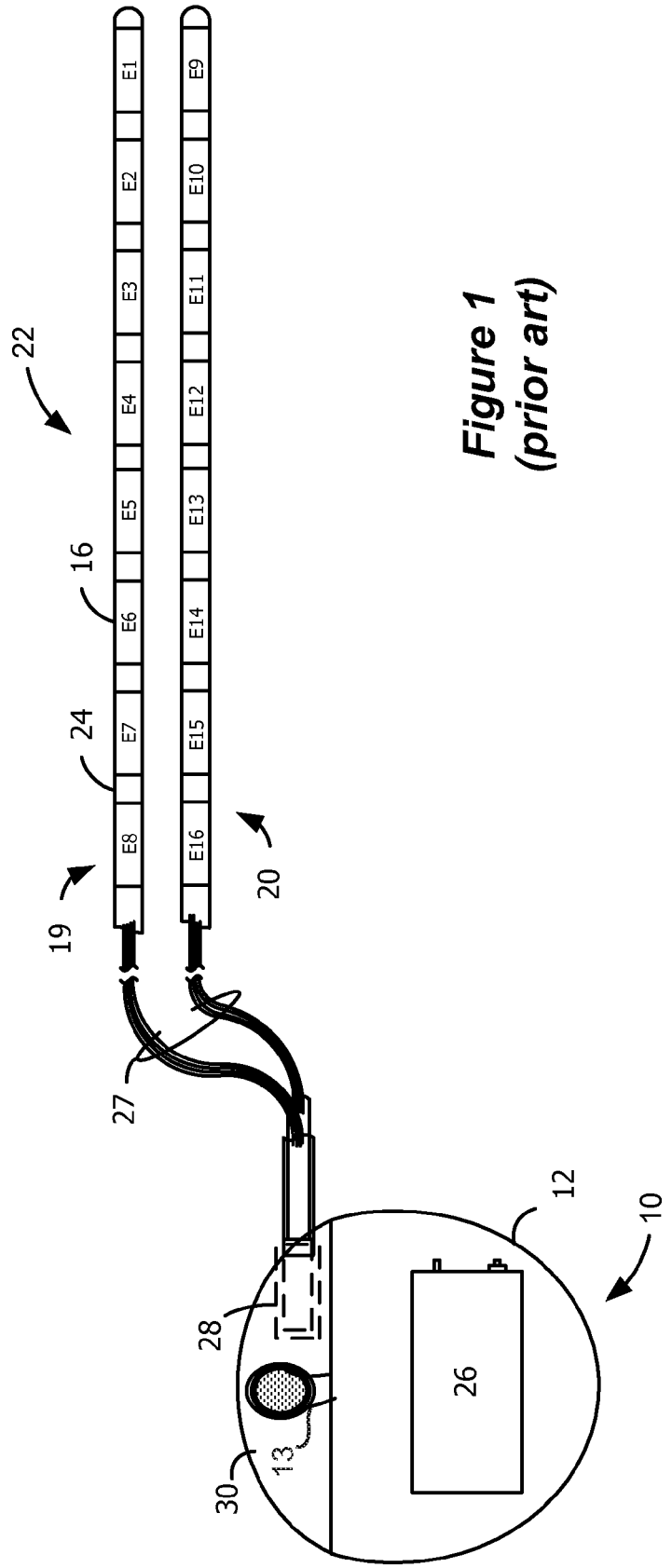
FIG. 1 shows an implantable pulse generator (IPG), and the manner in which an electrode array is coupled to the IPG in accordance with the prior art.
Figure 2:
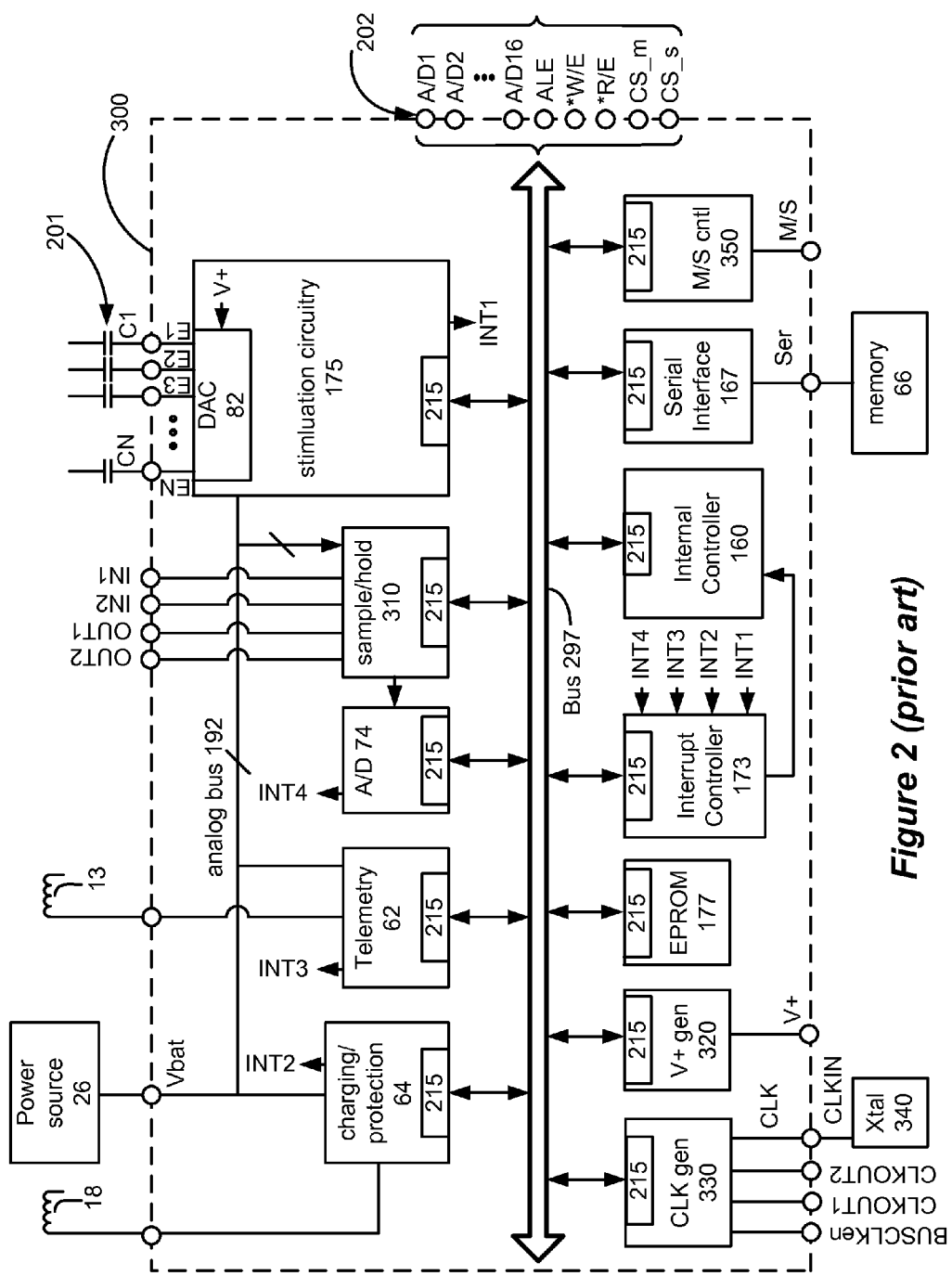
FIG. 2 shows an Application Specific Integrated Circuit (ASIC) used in an IPG in accordance with the prior art, in which an off-chip crystal oscillator is used to provide the clock signal for the ASIC.

Having a clock signal with a precise frequency is important to many different functions on the ASIC 300 and within the IPG 10. For example, the clock signal is used as the time basis for time stamp circuitry used to log the occurrence of certain data in the IPG 10, which can be telemetered externally from the IPG 10 for review. If the frequency of the clock is off, so too will the time basis of the logged data. The clock signal is also used as the time basis for modulating and demodulating data in the telemetry circuitry (see FIG. 2, 62). Therefore, if the frequency of the ASIC's clock signal is off, communications to and from the IPG 10 can be adversely affected.

Figure 3:
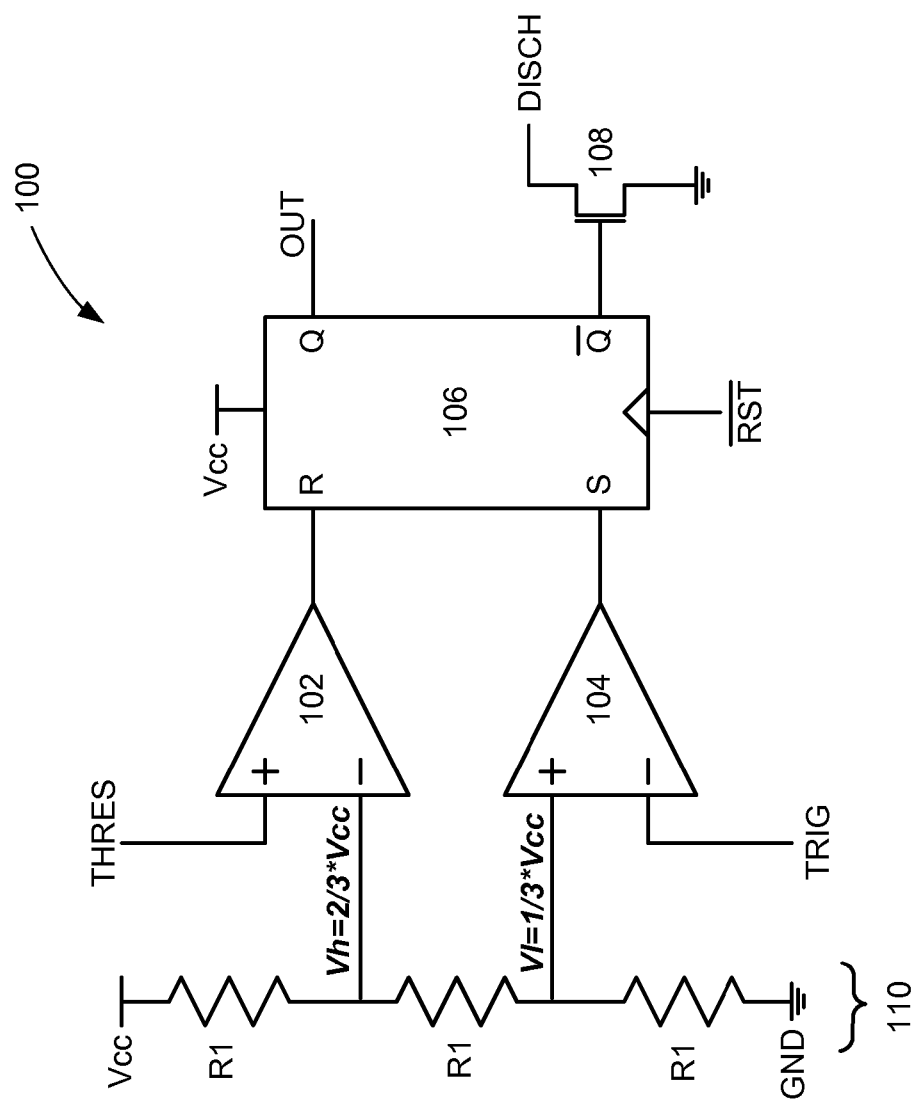
FIG. 3 shows a prior art timer circuit.

One option to consider as a candidate for integrated clocking circuitry is based on the well-known 555 Timer Integrated Circuit (IC), such as is described at http://en.wikipedia.org/wiki/555_timer, and which is included with this filing and is incorporated herein by reference. The internal circuitry of the 555 timer circuit 100 is shown in FIG. 3. Timer circuit 100 comprises a resistor ladder 110 comprising three resistors R1, which divide the power supply voltage (Vcc) to produce two reference voltages, Vh and Vl. Because each of resistances R1 are the same (5 k-ohms), these reference voltages are equally spaced between Vcc and ground, i.e., Vh=⅔Vcc, and Vl=⅓Vcc. Also included within the timer circuit 100 are two comparators 102 and 104, whose outputs are coupled to the inputs of toggle circuitry, such as an SR flip flop 106. Input signals THRES and TRIG are also input to the comparators 102 and 104 with the following results: if THRES>Vh, comparator 102 resets the flip flop 106 at input R, and output Q (OUT) goes low; if TRIG<Vl, comparator 104 sets the flip flop at input S, and output Q (OUT) goes high. Inverted output *Q takes the opposite state of Q, and thus turns on transistor 108 when the flip flop 106 is reset, thus shorting node DISCH to ground. Conversely, transistor 108 is turned off when the flip flop 106 is set, thus decoupling node DISCH.

Figure 4:
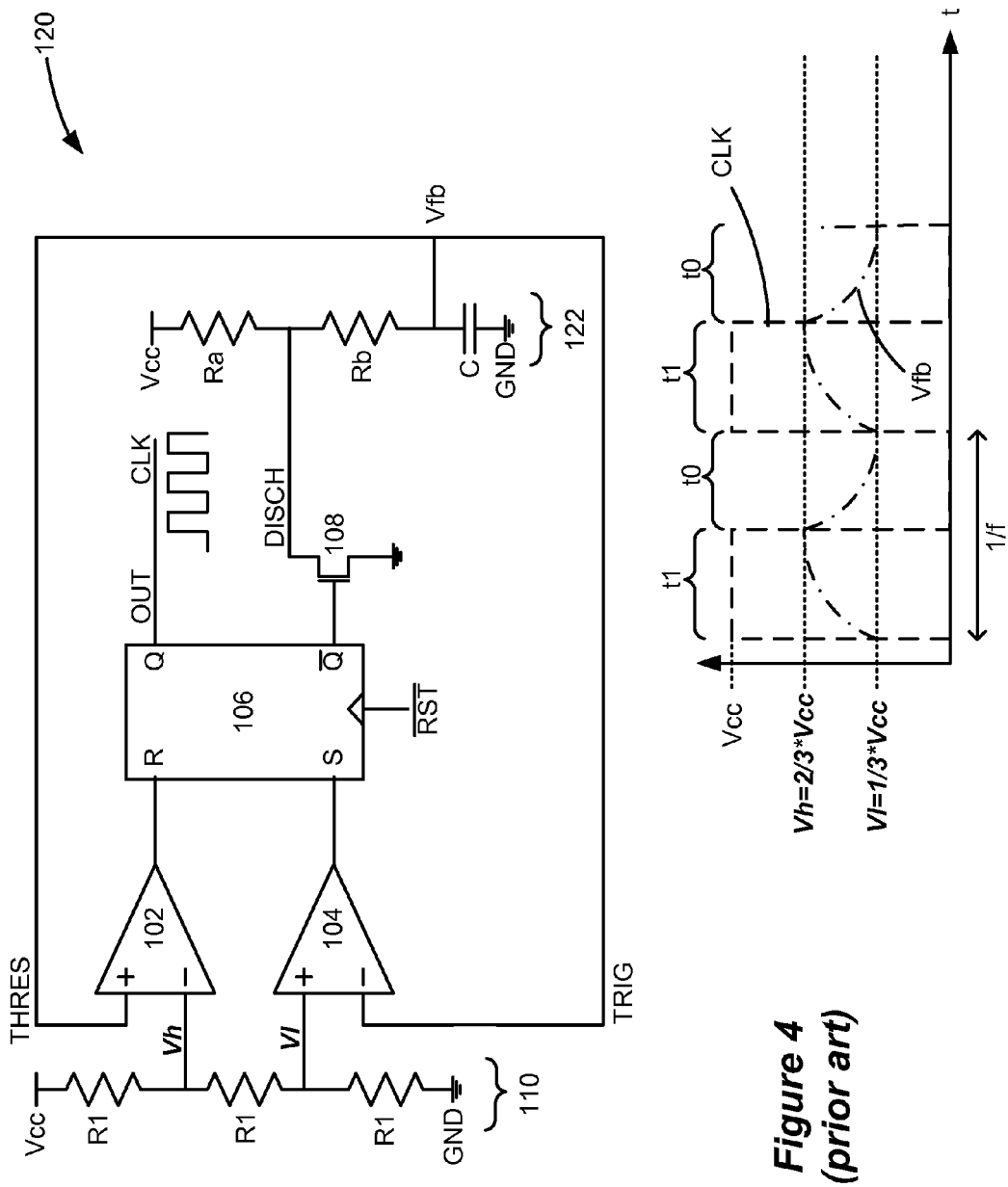
FIG. 4 shows the timer circuit of FIG. 3 configured in an stable mode to produce a clock signal in accordance with the prior art.

As the above-incorporated Wikipedia page describes, the 555 timer circuit 100 can be used in monostable, bistable, or astable modes. Configuration in the astable mode is shown in FIG. 4. Astable timer circuitry 120 operates to issue a free running clock signal, CLK, at output OUT. Added to the basic timer circuitry 100 of FIG. 3 is an RC circuit 122, comprising a serial connection of two resistors Ra and Rb and a capacitor C. A node, Vfb, is monitored in the RC circuit 122, and fed back to the THRES and TRIG inputs. When feedback signal Vfb equals Vl, comparator 104 sets the flip flop 106, Q (OUT) goes high, setting CLK to a first logic state (i.e., Vcc) and transistor 108 is turned off. This allows Vfb to rise in accordance with the time constant provided by Ra, Rb, and C. When Vfb later equals Vh, comparator 102 resets the flip flop 106, Q (OUT) goes low, stetting CLK to a second logic state (i.e., ground) and transistor 108 is turned on. Turning transistor 108 on shorts Rb and C to ground, and thus Vfb decreases in accordance with the time constant provided by Rb and C. Eventually, Vfb will once again equal Vl, and this cycle repeats.

The overall effect of astable timer circuit 120 is that Vfb varies between Vh and Vl (i.e., between ⅓Vcc and ⅔Vcc) as the RC circuit 122 charges and discharges, and the production of a clock signal at OUT. The frequency, f, of the clock signal is determined by selecting components Ra, Rb, and C of particular values to change the rate at which Vfb charges and discharges. Higher components values decrease the frequency, and lower values increase the frequency. Specifically, the frequency equals: $f=1/[\ln(2)*C*(Ra+2*Rb)]$.

Use of the astable timer circuit 120 is reasonable to consider as a candidate for integration within the ASIC 300 to generate a clock signal for an IPG application. Such circuitry 120 produces a clock signal with a frequency that is relatively insensitive to temperature, in particular because the resistors Ra and Rb and capacitor C in the RC circuitry 122 that set the frequency are relatively temperature independent. Such circuitry 120 can also start generating a stable clock signal within a few cycles, and thus much quicker than does a crystal.

However, the inventors also perceive some problems in integrating the astable timer circuit 120 into an ASIC 300. First, to set the astable timer circuit 120 to produce a clock signal with a particular frequency, it is generally required to use precision components in the RC circuit 122. This is difficult to do in an integrated solution as it is generally difficult to produce precision components on an integrated circuit due to manufacturing variability. As a result, the RC circuit 122 components used in traditional astable timer circuits 120 are generally discrete components provided off chip, which belies a fully integrated solution. Even if precision off-chip components are used (0.1% tolerance), the variance in the frequency produced may still be unacceptable for inclusion in an IPG 10.

Second, the astable timer circuit 120 does not produce a square wave clock signal having a 50% duty cycle. This is because different components in the RC circuit 122 are implicated during the charging and discharging phases. During the charging of the RC circuit 122, i.e., when Q (Out) is high, both resistors Ra and Rb are used in conjunction with capacitor C to set the charging rate, yielding a high time of: $t1=\ln(2)*(Ra+Rb)*C$. By contrast, during discharging of the RC circuit 122, i.e., when Q (OUT) is low, transistor 108 is on, which effectively removes resistor Ra from the circuit. This yields a low time $t0=\ln(2)*(Rb)*C$ that is smaller than the high time t1. In other words, the duty cycle of the clock signal is greater than 50%. This is generally not desirable in an ASIC 300 used in an IPG 10, as certain circuits may trigger off of rising or falling edges of the clock, and thus such timing would be asymmetrical.

Third, power draw in a traditional astable timer circuit 120 is significant, due in part to the relatively low resistances (R1=5 k-ohms) provided in the resistor ladder 110. The circuit 120 thus draws power on the order of tens of milliWatts, which is not suitable in an IPG application in which it is desirable to preserve battery power to reduce the need for frequent external charging of the IPG's battery.

Finally, the inventors notice that the frequency of the clock signal produced by the astable timer circuit 120 is sensitive to variations in the power supply voltage, Vcc. This is particularly due to the use of Vcc to set the threshold voltages Vh and Vl in the resistor ladder 110. As Vcc rises or falls, Vh and Vl will likewise rise or fall, which respectively decreases or increases the frequency of the clock signal. Vcc, depending on how it is produced, may also be dependent on temperature, which would also affect Vh and Vl, and hence the clock signal frequency.

Figure 5:
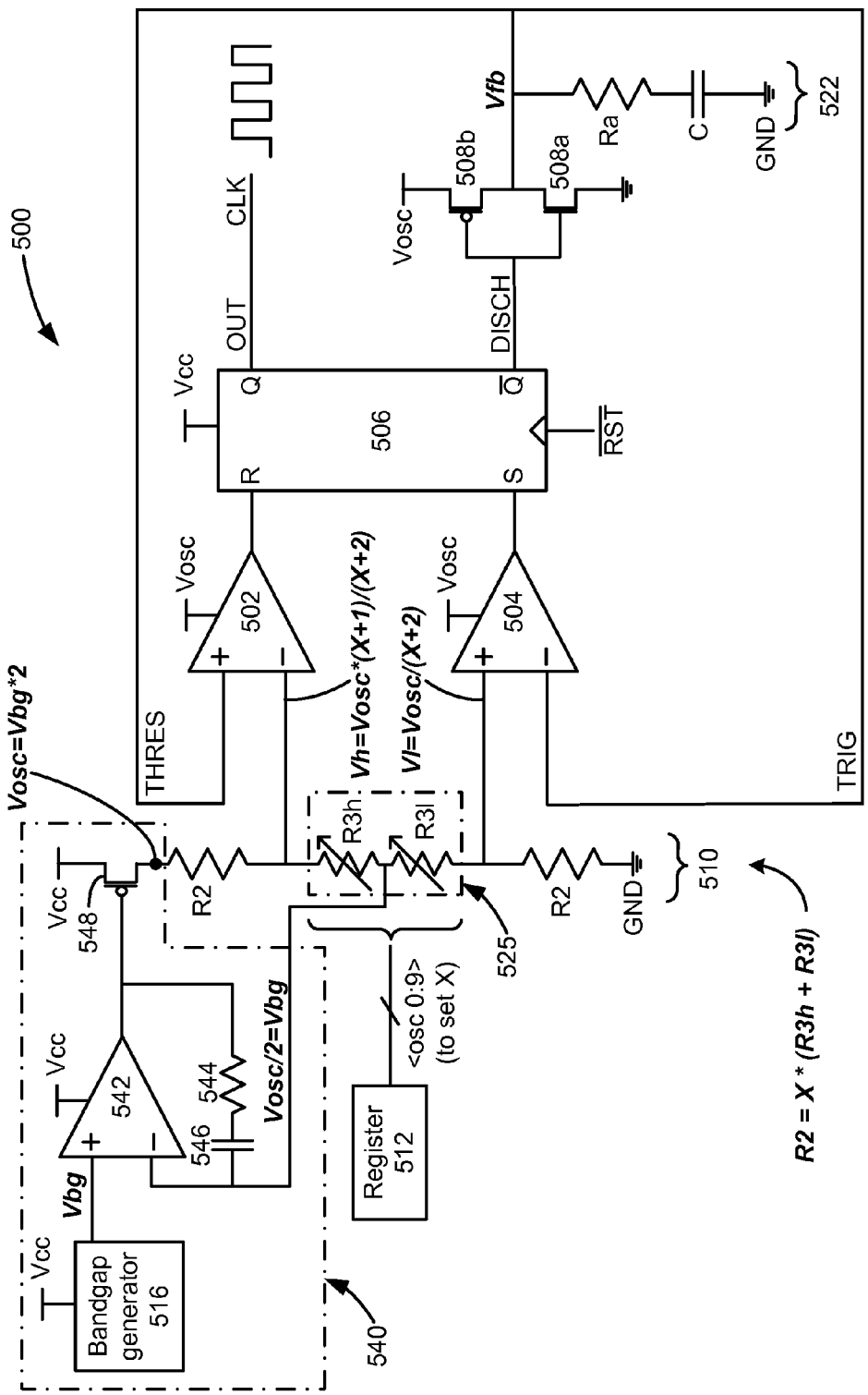
FIG. 5 shows an example of an improved astable timer circuit according to the invention.

The inventors have improved upon the astable timer circuit 120 of FIG. 4 in a manner which makes the circuit completely integratable on an IC such as ASIC 300, and one example of such improved circuit 500 is shown in FIG. 5. The astable timer circuit 500, like circuit 120 of FIG. 4, contains two comparators 502 and 504 which receive threshold voltages Vh and Vl from a resistor ladder 510. Circuit 500 also contains an RC circuit 522 comprising a single resistor Ra and capacitor C, which through charging and discharging provide a feedback signal Vfb back to the comparators 502 and 504. As before, the comparators 502 and 504 reset and set the flip flop 506, which produces a clock signal at Q (OUT). In this sense, the astable timer circuit 500 operates generally as did the astable timer circuit of FIG. 4.

However, circuit 500 contains modifications to improve performance and to address some of the aforementioned drawbacks of circuit 120 of FIG. 4. First, the components R and C in the RC circuit 522 are not precision components, and are merely fabricated on-chip components in the ASIC 300 whose values may vary from chip to chip. This lack of precision is acceptable, because RC circuit 522 is only used to provide a rough value for the desired frequency f of the clock signal. If the circuit 500 once fabricated does not produce a clock signal of the correct frequency, the frequency can be trimmed.

Such trimming occurs via a modification to the resistor ladder 510. As before, the resistor ladder 510 comprises a voltage divider which is used to set the threshold voltages Vh and Vl. However, the middle resistance 525 in the ladder 510 is adjustable, and is split into two equal resistances R3$h$ and R3$l$. The values for R3$h$ and R3$l$ are set, in this example, using ten trimming bits <osc 0:9>, which are sent from a 10-bit register 512. The use of ten trimming bits is merely one example, and other numbers of bits or other manners of trimming R3$h$ and R3$l$ can be used as well.

Figure 6:
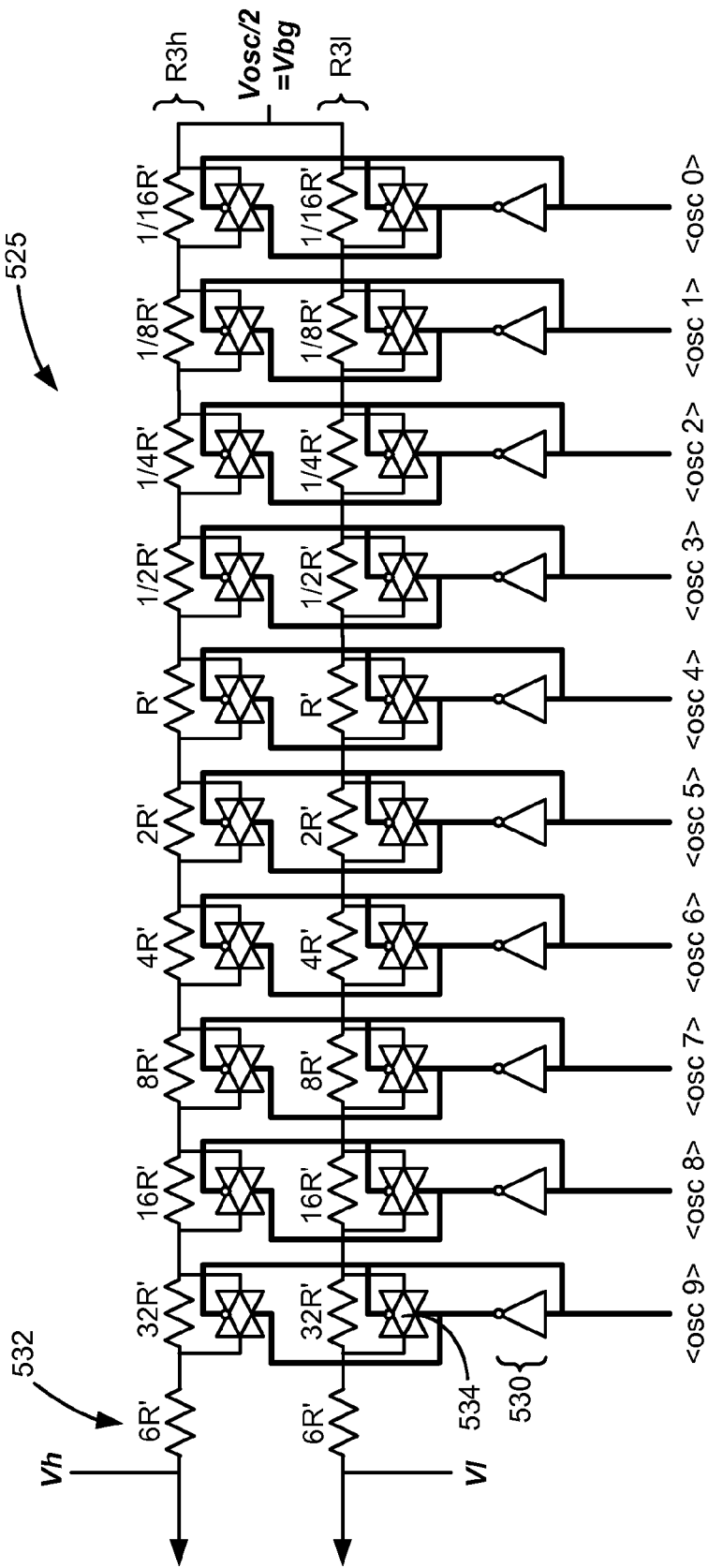
FIG. 6 shows an adjustable resistance useable in the improved circuit of FIG. 5.

A structure for middle resistance 525, i.e., R3$h$+R3$l$, is shown in FIG. 6, and includes serially-connected resistors. The resistors in this example are binary multiples of a resistance R', although this is not strictly necessary. In the depicted example, the first resistor is 32 times the value of R', the second is 16 times R', and so on, down to smaller fractions, such that the last resistor is ⅟₁₆ R'. Each resistor is spanned by a transmission gate 534, which when activated can bypass that resistor and therefore disclude it from the resistance 525. Each trimming bit <osc> controls the transmission gates 534 for similarly-sized resistors in R3$h$ and R3$l$. Inverters 530 are used to provide both inverted and non-inverted versions of the trimming bits necessary to control the P and N transistors in the transmission gates 534. Fixed resistances 532 not selectable via the trimming bits can also be included in the resistance 525 to guarantee a minimum resistance, such as the 6R' resistors included in both R3$h$ and R3$l$.

Asserting different values for the trimming bits allows the resistance 525 to be tailored. For example, if only <osc3> is asserted, both of the ½R' resistors in R3$h$ and R3$l$ will be included in the resistance 525, for a total resistance of 2*(6R'+½R')=13R'. In another example, asserting <osc6> and <osc1> will yield a total resistance of 2*(6R'+4R'+⅛R'), or 20.25Rc. Thus, by asserting different trimming bits, the total resistance 525 can be as low as 12R' (no trimming bits asserted, and therefore only fixed resistances 532 included), and can be incremented in ⅛R' steps to approximately 140R' (all trimming bits asserted). The value of R' is typically chosen to be relatively small in comparison to resistors R2 in the resistor ladder 510. For example 60*R'=R2, although again this can be varied.

Returning to FIG. 5, the total resistance 525 once set by the trimming bits can be described in terms of a scalar X relative to R2, i.e., R2=X*(R3$h$+R3$l$). Using the example resistance values provided above, X can range from about 0.2 to 2.3 depending on which trimming bits are asserted. However, this is merely one example; resistance 525 can be formed and made variable in many other manners.

Figure 7:
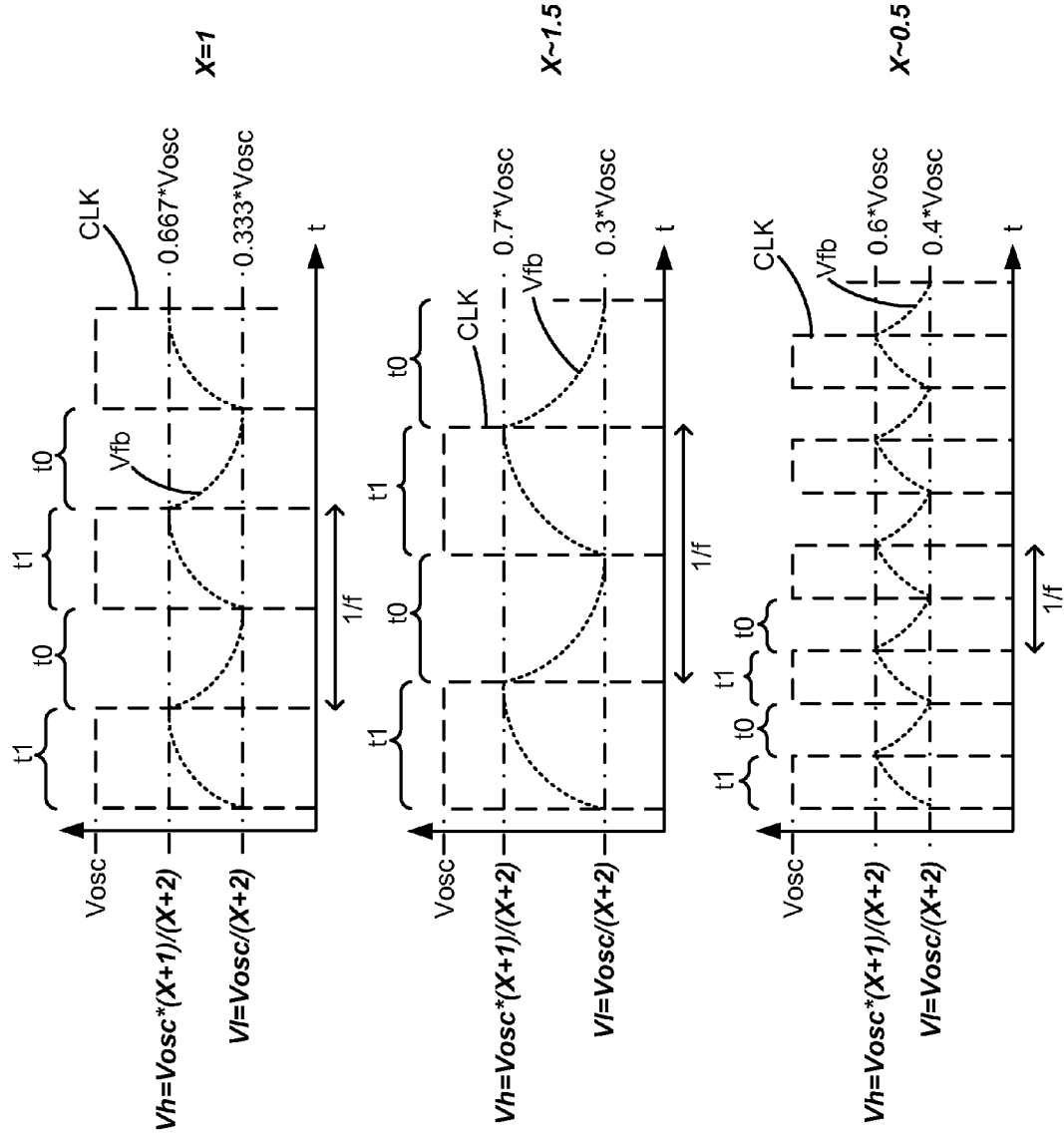
FIG. 7 shows the production of clock signals with different frequencies as the resistance of FIG. 6 is adjusted.

As also shown in FIG. 5, threshold voltages Vh and Vl can be expressed in terms of X and in terms of Vosc, a power supply voltage which will be described subsequently. Because each of resistors R3$h$ and R3$l$ are trimmed similarly, the overall effect of changing X is to symmetrically change the values of Vh and Vl around a midpoint power supply value Vosc/2. This is shown in FIG. 7. In the top diagram, X=1, meaning that R3$h$+R3$l$=R2. For this value of X, Vh=⅔Vosc and Vl=⅓Vosc. If X is increased (i.e., if R3$h$+R3$l$>R2), for example to about 1.5 in the middle diagram, Vh and Vl are both shifted about midpoint ½Vosc to about 0.7Vosc and 0.3Vosc. If X is decreased (i.e., if R3$h$+R3$l$<R2), for example to about 0.5 in the bottom diagram, Vh and Vl are again both shifted about midpoint ½Vosc to about 0.6Vosc and 0.4Vosc.

Note the effect changing X has on the resulting frequency, f, of the square wave. When X is increased and Vh and Vl are pushed farther apart, the frequency decreases. By contrast, when X is decreased and Vh and Vl are brought closer together, the frequency increases. Note also that the shape of Vfb doesn't change, because how quickly Vfb charges or discharges is dictated by the value of the components in the RC circuit 522, Ra and C. The resulting frequency of the clock signal can be expressed as a function of X as f=1/[2*Ra*C*ln(X+1)].

Thus, by tailoring the trimming bits <osc> (and hence X) to desired values, the frequency of the square wave can be set to a correct and precise value, even if the value of the components Ra and C in the RC circuit 522 are imprecise and vary from chip to chip. Such tailoring of the trimming bits would normally occur during manufacture of the IPG 10 or the ASIC 300 into which circuit 500 is integrated. This would typically involve chip-by-chip testing to try different combinations of the trimming bits to see which combination yields the desired frequency for ASIC clock signal, for example 100 kHz. Once determined, the values for the trimming bits are stored in register 512 on the ASIC 300 and used thereafter in the IPG 10. The register 512 preferably comprises a non-volatile memory, such as EPROM, flash EPROM, or one-time-programmable fuses or antifuses. If register 512 does not comprise one-time programmable structures, the values of the trimming bits can also be changed after manufacturing if necessary, for example, as controlled by telemetry from an external device.

As noted, how quickly node Vfb charges or discharges is dictated by the value of the components in the RC circuit 522. Circuit 500 of FIG. 5 improves upon the prior art circuit 120 of FIG. 4 in this regard, because the same components in the RC circuit 522 are used during both the charging and discharging phases. During charging, i.e., when the flip flop 506 is set and *Q is low, P-channel transistor 508$b$ is turned on, thus charging Vfb in accordance with the time constant of Ra and C. During discharging, i.e., when the flip flop 506 is reset and *Q is high, N-channel transistor 508$b$ is turned on, thus discharging Vfb, again in accordance with the time constant of Ra and C. One skilled in the art will recognize that transistors 508$a$ and 508$b$ comprise an inverter. Because the same RC time constant is involved in both the charging and discharging phases, and because Vh and Vl vary around a midpoint value, the produced clock signal has a 50% duty cycle where t1=t0=Ra*C*ln(X+1). As noted earlier, this is preferable particularly when the circuit 500 is integrated into an ASIC 300 which has circuits that use both the rising and falling edges of the clock signal.

In another improvement to the astable timer circuit 120 of FIG. 4, the astable timer circuit 500 of FIG. 5 is made to have a much lower power draw on the order of microWatts. This is due in large part to the adjustment of the resistances R2, R3$h$ and R3*l* in the resistor ladder 510 to higher values. For example, R2 can be on the order of several Mega-ohms or more, compared to 5 k-ohms in circuit 120.

Astable timer circuit 500 further improves on the astable timer circuit 120 of FIG. 4 by removing sensitivity to variations in the power supply, Vcc. As shown in FIG. 5, a Low Drop Out (LDO) regulator 540 is provided to generate a power supply, Vosc, for the majority of the components in circuit 500. In particular, Vosc is used as the power supply for the resistor ladder 510, as noted earlier. A center tap of the resistor ladder 510 between R3*h* and R3*l* is used to provide feedback to the LDO regulator 540 to keep Vosc at a stable level. Because the resistances above (R2+R3*h*) and below (R2+R3*l*) the center tap are the same, the voltage at the center tap is one-half of the power supply voltage, i.e., Vosc/2.

In the LDO regulator 540, the center tap is input to an operational amplifier 542, whose other input comprises a bandgap voltage, Vbg, a temperature-insensitive voltage provided by a bandgap generator 516. Bandgap generators 516 are well known, and Vbg typically equals 1.28V. Feedback of the output of the op amp 542 to the center tap via resistor 544 and capacitor 546 ensures that the center tap is held at reference input Vbg, i.e., Vosc/2=Vbg, and therefore Vosc=2*Vbg. Transistor 548 decouples Vosc from Vcc, and hence variations in Vcc will be rejected and thus not impact operation of the astable timer circuit 500. In other words, neither Vosc nor the frequency of the clock signal will appreciably vary with Vcc. Moreover, because Vbg is generally insensitive to temperature, Vosc will likewise be relatively temperature independent. It is estimated that the frequency of the clock signal produced by astable timer circuit 500 will vary at less than 100 ppm/oC, which is suitably precise for the temperature ranges the ASIC 300 and IPG 10 will experience.

In FIG. 5, SR flip flop 506 is powered by the main power supply Vcc so that the resulting clock signal CLK will also be referenced to this voltage, as the rest of the ASIC 300 would expect. Because the comparators 502 and 504 preceding the SR flip flop are powered by a different power supply, Vosc, some amount of level translation is necessary, although such details are not shown and are within the knowledge of one skilled in the art. Alternatively, the SR flip flop 506 could also be powered by Vosc, with the resulting clock signal level translated relative to Vcc thereafter and before dissemination to the remainder of the ASIC 300.

Figure 8:
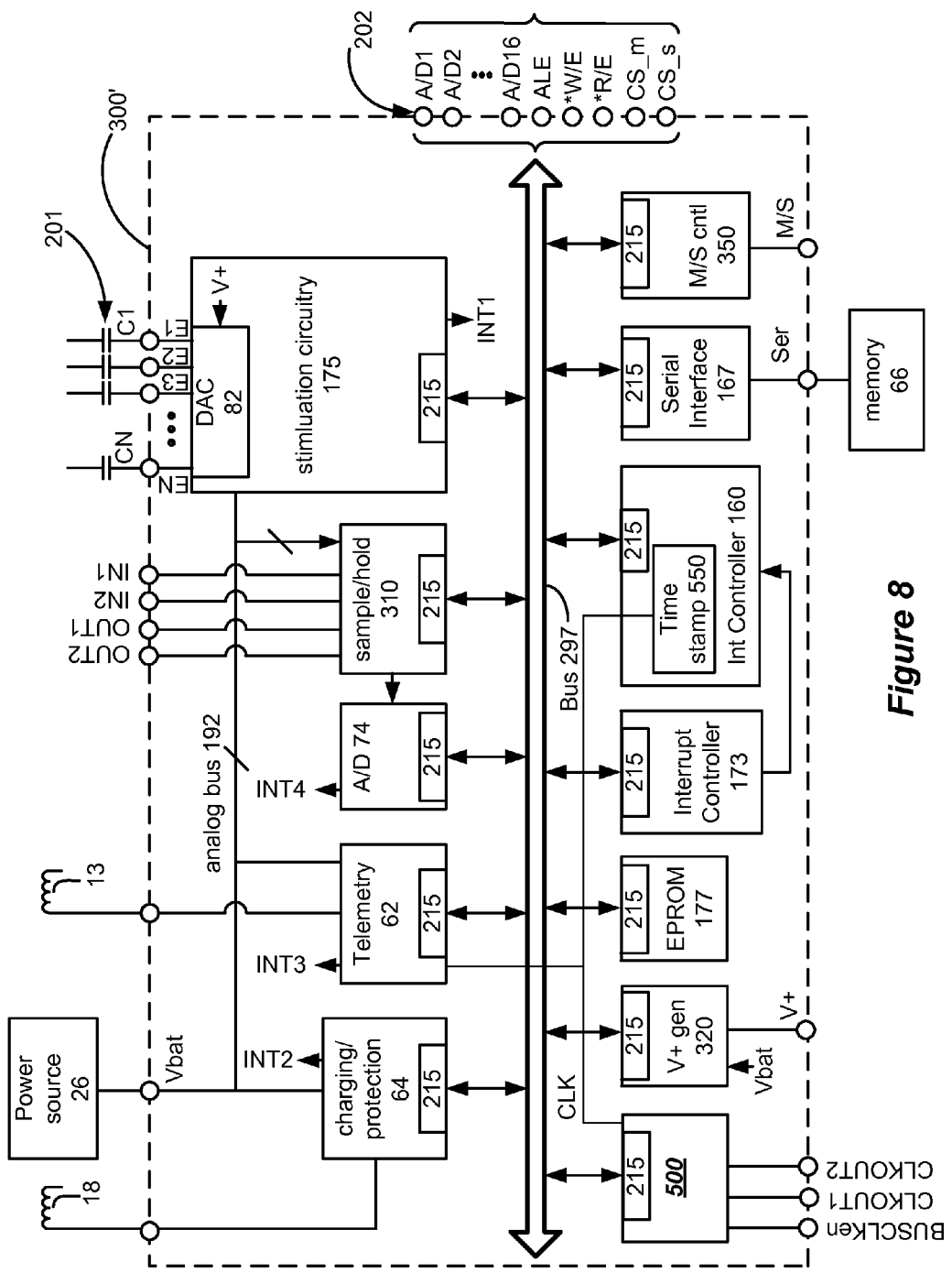
FIG. 8 shows an ASIC useable in an IPG having the integrated therein the improved astable timer circuit.

An ASIC 300' incorporating the disclosed astable timer circuit 500 for producing a clock signal, CLK, is shown in FIG. 8. While CLK would be widely disseminated around the ASIC 300' and used for many purposes, it is only shown in FIG. 8 with reference to certain modules mentioned earlier that have a particular need for precise timing. Thus, CLK is sent to the telemetry circuit 62, which can use this signal as the time basis for modulation and demodulation of data, thereby ensuring that the wireless frequency of received and transmitted data is well matched with that used in the external device with which it communicates. Also shown is receipt of CLK at time stamp circuitry 550 within the ASIC's 300' internal controller 160. As mentioned earlier, time stamp circuitry 550 uses the clock signal to time stamp certain data in the IPG 10 so that it can be stored and transmitted externally for review.

Figure 9:
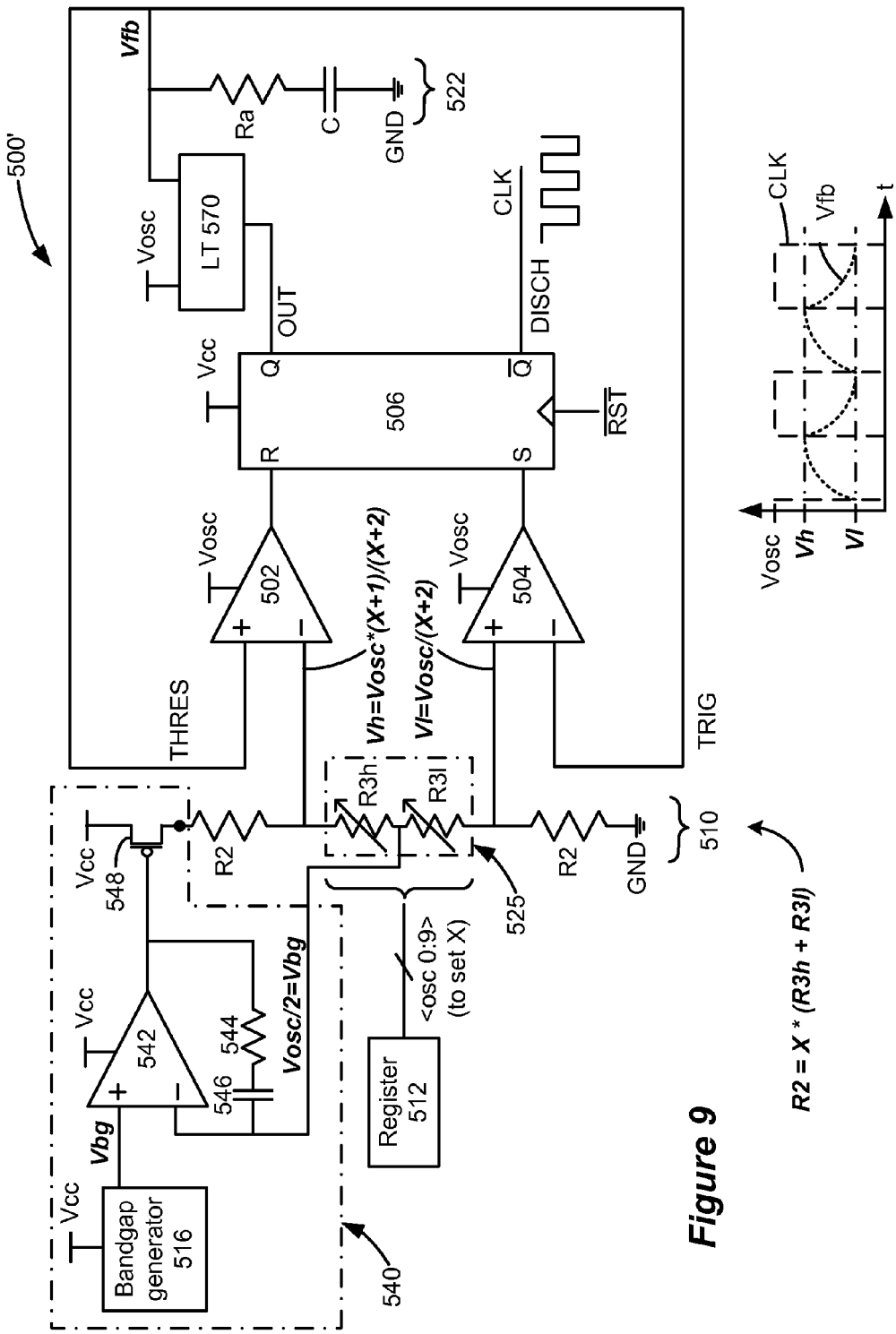
FIG. 9 shows a modification to the astable timer circuit of FIG. 5 according to the invention.

FIG. 9 shows a modification 500' to the astable timer circuit in which the clock signal CLK is generated at node DISCH (*Q), and where the RC circuit 522 is instead coupled to the OUT node (Q). In this modification, the clock signal is set to logic state high (to Vcc) when Vfb exceeds Vh, which also causes the RC circuit 522 to discharge. Conversely, the clock signal is set to logic state low (to ground) when Vfb falls below Vl, which also causes the RC circuit 122 to charge. This is different from circuit 500 of FIG. 5, because in that that circuit, setting the clock signal high charged RC circuit 522, while setting the clock signal low discharged the RC circuit (see FIG. 7). In this modification, the input to the RC circuit 522 doesn't need to be inverted (compare transistors 508*a* and 508 in FIG. 5), although it is beneficial to level translate OUT to the Vosc domain using a level translator 570 so that Vfb will be properly referenced when feedback to the comparator circuitry. Otherwise, circuit 500' act as does circuit 500 described earlier.

One skilled in the art will understand that toggle circuitry for producing the clock signal can comprise circuits other than SR flip flops, and therefore that toggle circuitry should comprise any circuitry capable of producing a clock signal in accordance with the technique described herein, which circuitry may involve other types of flip flops or different structures.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry for generating a clock signal, comprising:
   a high reference voltage and a low reference voltage;
   toggle circuitry configured to produce the clock signal, wherein the toggle circuitry is configured to set the clock signal to a first logic state when a feedback voltage is lower than the low reference voltage, and wherein the toggle circuitry is configured to set the clock signal to a second logic state when the feedback voltage is higher than the high reference voltage; and
   an RC circuit configured to produce the feedback voltage, wherein the feedback voltage charges when the clock signal is in one of the first or second logic states, and discharges when the clock signal is in the other of the first or second logic states,
   wherein the high and low reference voltages are simultaneously adjustable symmetrically around a midpoint of a first power supply voltage to adjust a frequency of the clock signal.

2. The circuitry of claim 1, further comprising comparator circuitry configured to compare the feedback voltage to the high and low reference voltages, and to inform the toggle circuitry when the feedback voltage is lower than the low reference voltage, and when the feedback voltage is higher than the high reference voltage.

3. The circuitry of claim 1, wherein the first logic state comprises a high logic state, and wherein the second logic state comprises a low logic state.

4. The circuitry of claim 1, wherein the first logic state comprises a low logic state, and wherein the second logic state comprises a high logic state.

5. The circuitry of claim 1, further comprising a voltage divider configured to produce the first and second reference voltages from a first power supply voltage.

6. The circuitry of claim 5, further comprising a regulator configured to produce the first power supply voltage from a second power supply voltage.

7. The circuitry of claim 6, wherein the regulator comprises a bandgap generator, and wherein the first power supply is insensitive to temperature.

8. The circuitry of claim 5, wherein the voltage divider comprises a first resistance between the first power supply voltage and the high reference voltage, a second resistance between the high and low reference voltages, and a third resistance between the low reference voltage and a second power supply voltage.

9. The circuitry of claim 8, wherein the second power supply voltage is ground.

10. The circuitry of claim 8, wherein the second resistance is adjustable to simultaneously adjust the high and low reference voltages symmetrically around the midpoint of the first power supply voltage.

11. The circuitry of claim 8, wherein the first and third resistances are equal.

12. The circuit of claim 1, further comprising a register, and wherein the high and low reference voltages are simultaneously adjustable in accordance with the data stored in the first register.

13. The circuitry of claim 1, wherein the toggle circuitry comprises a flip flop.

14. The circuitry of claim 13, wherein the clock signal and the RC circuit are coupled to inverted outputs of the flip flop.

15. The circuitry of claim 13, wherein the flip flop comprises an SR flip flop.

16. The circuitry of claim 1, wherein the RC circuit comprises a serial connection of a resistor and a capacitor.

17. The circuitry of claim 1, wherein the circuitry is integrated on an integrated circuit.

18. Circuitry for generating a clock signal, comprising:
an integrated circuit, the integrated circuit comprising:
a voltage divider configured to produce a high reference voltage and a low reference voltage from a first power supply voltage;
comparator circuitry configured to compare a feedback voltage to the high and low reference voltages, wherein the comparator circuitry comprises a first output configured to indicate whether when the feedback voltage is lower than the low reference voltage, and a second output configured to indicate whether the feedback voltage is higher than the high reference voltage;
toggle circuitry configured to receive the first and second outputs and to produce the clock signal, wherein the toggle circuitry is configured to set the clock signal to a first logic state when the first output is asserted, and wherein the toggle circuitry is configured to set the clock signal to a second logic state when the second output is asserted; and
an RC circuit configured to produce the feedback voltage, wherein the feedback voltage charges when the clock signal is in one of the first or second logic states, and discharges when the clock signal is in the other of the first or second logic states,
wherein the voltage divider is adjustable to simultaneously adjust both the high and low reference voltages symmetrically around a midpoint of the first power supply voltage to adjust a frequency of the clock signal.

19. The circuitry of claim 18, wherein the comparator circuitry comprises a first comparator configured to compare the high voltage with the feedback signal to produce the first output, and a second comparator configured to compare the low voltage with the feedback signal to produce the second output.

20. The circuitry of claim 18, wherein the voltage divider comprises a resistor ladder comprising a first resistance between the first power supply voltage and the high reference voltage, a second resistance between the high and low reference voltages, and a third resistance between the low reference voltage and ground.

21. The circuitry of claim 20, wherein the second resistance is adjustable to simultaneously adjust the high and low reference voltages symmetrically around the midpoint of the first power supply voltage.

22. The circuitry of claim 21, wherein the second resistance is adjustable in accordance with a plurality of bits.

23. The circuit of claim 18, wherein the integrated circuit further comprises a register, and wherein the high and low reference voltages are simultaneously adjustable in accordance with the data stored in the first register.

24. The circuitry of claim 18, wherein the toggle circuitry comprises a flip flop.

25. The circuitry of claim 24, wherein the clock signal and the RC circuit are coupled to inverted outputs of the flip flop.

26. The circuitry of claim 24, wherein the flip flop comprises an SR flip flop.

27. The circuitry of claim 18, wherein the integrated circuit further comprises a regulator configured to produce the first power supply voltage from a second power supply voltage.

28. The circuitry of claim 27, wherein the regulator comprises a bandgap generator, and wherein the first power supply is insensitive to temperature.

29. The circuitry of claim 18, wherein the RC circuit comprises a serial connection of a resistor and a capacitor.

30. The circuitry of claim 18, wherein the integrated circuit further comprises stimulation circuitry coupleable to a plurality of electrodes for stimulation of tissue of a patient in which the circuitry is implanted.

31. The circuitry of claim 18, wherein the integrated circuit is configured for inclusion in an implantable medical device.

\* \* \* \* \*